US010358440B2

(12) United States Patent
Desai et al.

(10) Patent No.: US 10,358,440 B2
(45) Date of Patent: Jul. 23, 2019

(54) PROCESS FOR THE PREPARATION OF BREXPIPRAZOLE AND INTERMEDIATES THEREOF

(71) Applicant: CADILA HEALTHCARE LIMITED, Ahmedabad, Gujarat (IN)

(72) Inventors: Sanjay Jagdish Desai, Ahmedabad-Gujarat (IN); Jayprakash Ajitsingh Parihar, Ahmedabad-Gujarat (IN); Alpesh Pravinchandra Shah, Ahmedabad-Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 16/274,352

(22) Filed: Feb. 13, 2019

(65) Prior Publication Data

US 2019/0177309 A1 Jun. 13, 2019

Related U.S. Application Data

(62) Division of application No. 15/585,605, filed on May 3, 2017.

(30) Foreign Application Priority Data

May 3, 2016 (IN) .............................. 201621015388
May 30, 2016 (IN) .............................. 201621018551
Mar. 18, 2017 (IN) .............................. 201721009474

(51) Int. Cl.
| C07D 409/12 | (2006.01) |
| C07D 487/10 | (2006.01) |
| C07D 409/14 | (2006.01) |
| C07D 333/54 | (2006.01) |
| C07D 247/02 | (2006.01) |
| C07D 401/12 | (2006.01) |
| A61K 9/14 | (2006.01) |
| A61K 31/496 | (2006.01) |
| B01D 9/02 | (2006.01) |

(52) U.S. Cl.
CPC .............. *C07D 409/14* (2013.01); *A61K 9/14* (2013.01); *A61K 31/496* (2013.01); *C07D 247/02* (2013.01); *C07D 333/54* (2013.01); *C07D 401/12* (2013.01); *C07D 409/12* (2013.01); *C07D 487/10* (2013.01); *B01D 9/02* (2013.01)

(58) Field of Classification Search
CPC ............................ C07D 409/12; C07D 487/10
See application file for complete search history.

(56) References Cited

U.S. PATENT DOCUMENTS

| 5,922,355 | A | 7/1999 | Parikh et al. |
| 7,888,362 | B2 | 2/2011 | Yamashita et al. |
| 2013/0143897 | A1 | 6/2013 | Bhutada et al. |
| 2013/0245069 | A1 | 9/2013 | Jacobson |
| 2014/0187782 | A1 | 7/2014 | Shinhama et al. |

FOREIGN PATENT DOCUMENTS

| CN | 105440026 A | 3/2013 |
| CN | 104829602 A | 8/2015 |
| CN | 104829603 A | 8/2015 |
| CN | 104844585 A | 8/2015 |
| CN | 105061414 A | 11/2015 |
| CN | 105175401 A | 12/2015 |
| CN | 105399736 A | 3/2016 |
| CN | 105461703 A | 4/2016 |
| CN | 105461704 A | 4/2016 |
| CN | 105541819 A | 5/2016 |
| CN | 105859703 A | 8/2016 |
| CN | 104844586 A | 12/2016 |
| CN | 106188023 A | 12/2016 |
| WO | 2013015456 A1 | 1/2013 |
| WO | 2013/162046 A1 | 10/2013 |
| WO | 2015054976 A1 | 3/2015 |
| WO | 2017025987 A1 | 2/2017 |

OTHER PUBLICATIONS

Shabir et al, Journal of Validation Technology, p. 29-37, 2004.

*Primary Examiner* — Emily A Bernhardt
(74) *Attorney, Agent, or Firm* — Ladas & Parry LLP (57) ABSTRACT

The present invention relates to Brexpiprazole having a purity of about 99.5% or more by area percentage of HPLC, having total impurities not more than 0.5% relative to brexpiprazole as measured by area percentage of HPLC, and having less than 0.1% 1-(benzo[b]thiophen-4-yl)piperazine or a salt thereof relative to brexpiprazole by area percentage of HPLC. The present invention also provides a composition comprising brexpiprazole having 1-(benzo[b]thiophen-4-yl)-piperazine or a salt thereof in an amount less than about 0.1% relative to brexpiprazole by area percentage of HPLC and process for the preparation of brexpiprazole.

8 Claims, 5 Drawing Sheets

PROCESS FOR THE PREPARATION OF BREXPIPRAZOLE AND INTERMEDIATES THEREOF

CROSS REFERENCE APPLICATIONS

This application is a Divisional of U.S. application Ser. No. 15/585,605 filed May 3, 2017, which claims the benefit of Indian Applications Nos. 201621015388 filed May 3, 2016, 201621018551 filed May 30, 2016, and 201721009474 filed Mar. 18, 2017, the content of which are incorporated herein by reference.

FIELD OF THE INVENTION

The field of invention relates to process for the preparation of brexpiprazole and intermediates thereof. In particular, the invention relates to the process for the preparation of pure brexpiprazole. The invention further relates to a pharmaceutical compositions comprising pure brexpiprazole for the treatment of patients with schizophrenia or for the use as an adjunctive therapy to antidepressants for the treatment of major depressive disorder (MDD).

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Brexpiprazole, an atypical antipsychotic, is available as REXULTI® (brexpiprazole) tablets. It was developed by Otsuka Pharm Co Ltd. Brexpiprazole is chemically known as 7-{4-[4-(1-benzothiophen-4-yl) piperazin-1-yl] butoxy}quinolin-2(1H)-one of Formula (I).

(I)

U.S. Pat. No. 7,888,362 B2 (US '362 B2) discloses brexpiprazole and process for its preparation. The brexpiprazole prepared by the process disclosed in US '362 B2 provides higher levels of impurities which are difficult to separate even by purifications mentioned therein. The brexpiprazole obtained by the process of US '362 B2 is having purity of 91.82% by HPLC, which upon purification by the methods reported therein provides a purity of 95.11% by HPLC. The starting material, compound of Formula (V) was found to the level of 1.0% after purification. Thus, the process disclosed in US '362 B2 provides brexpiprazole with higher impurity levels which may not be suitable for formulations.

International PCT Publication Nos. WO 2013/015456 A1, WO 2015/054976 A1 and WO 2017/025987A1 discloses processes for the preparation of brexpiprazole, intermediates and salts thereof.

International PCT Publication No. WO 2013/162046 A1 discloses dihydrate of 7-[4-(4-benzo[b]thiophen-4-yl-piperazin-1-yl)butoxy]-1H-quinolin-2-one or salt thereof and process for preparation thereof.

Chinese Publication Nos. CN 104829602 A, CN 104844585 A, CN 105061414 A, CN 105175401 A, CN 105399736 A, CN 105440026 A, CN 105461704 A, CN 105461703 A, CN 105541819 A, CN 105859703 A and CN 106188023 A discloses processes for the preparation of brexpiprazole and intermediates thereof.

Chinese Publication No. CN 104844586 A discloses amorphous brexpiprazole and a preparation method thereof.

Chinese Publication No. CN 104829603 A discloses crystal form A of brexpiprazole hydrochloride and process for preparation thereof.

The reported processes disclosed in the art involve several chemical steps and provide the product in a very low yield and higher impurity levels. This results into an expensive process for the preparation of the brexpiprazole and intermediates thereof.

In view of the above, the present invention provides a process for the preparation of pure brexpiprazole in high purity and having lower level of one or more impurities.

SUMMARY OF THE INVENTION

In one general aspect, there is provided brexpiprazole having a purity of about 99.5% or more by area percentage of HPLC.

In another general aspect, there is provided brexpiprazole having total impurities not more than 0.5% relative to brexpiprazole as measured by area percentage of HPLC.

In another general aspect, there is provided brexpiprazole having less than 0.1% 1-(benzo[b]thiophen-4-yl)piperazine or a salt thereof relative to brexpiprazole by area percentage of HPLC.

In general another aspect, there is provided brexpiprazole substantially free from one or more of: 7-(4-(4-(benzo[b]thiophen-4-yl)piperazin-1-yl)butoxy)-1-(4-(4-(benzo[b]-thiophen-4-yl)piperazin-1-yl)butyl)quinolin-2(1H)-one (impurity-S); 2,7-bis(4-(4-(benzo [b]thiophen-4-yl)piperazin-1-yl)butoxy)quinoline (impurity-T); or 7-(4-(4-(benzo[b]thiophen-4-yl) piperazin-1-yl)butoxy)-1,2-dihydroquinoline (impurity-U), relative to brexpiprazole by area percentage of HPLC.

In another general aspect, there is provided brexpiprazole having particle size d90 of about 100 μm or less.

In another general aspect, there is provided brexpiprazole having a purity of about 99.5% or more by area percentage of HPLC, prepared by a process comprising:

(a) reacting a compound 1-(benzo[b]thiophen-4-yl)piperazine hydrochloride of Formula (V) with 1,4-dibromobutane to obtain a spiro compound of Formula (III); and (V)

(III)

(b) reacting the spiro compound of Formula (III) with a compound 7-hydroxyquinolin-2(1H)-one of Formula (II),

(II)

to obtain the brexpiprazole.

In another general aspect, there is provided a process for the preparation of brexpiprazole, the process comprising:
(a) reacting a compound 7-(4-hydroxybutoxy)quinoline-2-(1H)-one of Formula (X) with an oxidizing agent to prepare a compound of Formula (A); and

(b) reacting the compound of Formula (A) with a compound 1-(benzo[b]thiophen-4-yl)piperazine of Formula (B),

(B)

to obtain the brexpiprazole.

In another general aspect, there is provided a process for the preparation of brexpiprazole, the process comprising:
(a) reacting a compound 7-hydroxyquinolin-2-(1H)-one of Formula (II) with a compound of Formula (S) to obtain a compound of Formula (R);

(II)

(R)

wherein X is OH, Cl, Br, I, —OCOCH$_3$.
(b) reacting the compound of Formula (R) with bis-(2-chloroethyl)amine hydrochloride of Formula (Q) to obtain a compound of Formula (P); and (c) reacting the compound of Formula (P) with benzo[b]thiophen-4-amine to obtain brexpiprazole.

In another general aspect, there is provided a crystalline Form A of brexpiprazole and process for the preparation thereof.

In another aspect, there is provided a crystalline Form B of brexpiprazole and process for the preparation thereof.

In another aspect, there is provided a pharmaceutical composition comprising brexpiprazole prepared by the processes of the present invention together with one or more pharmaceutically acceptable carriers, excipients or diluents.

DETAILED DESCRIPTION OF THE INVENTION

The present inventors have found that preparation of brexpiprazole by the process of the present invention, the formation of impurities can be minimized and better purity and chemical stability can be achieved. The inventors have developed a process for the preparation of brexpiprazole, which exhibit control of impurities and stability under various stress conditions.

As used herein the term "obtaining" means isolating brexpiprazole by the ways of filtration, filtration under vacuum, centrifugation, and decantation. The product may be preceded for further steps with or without isolation and with or without drying in case of the product was isolated.

As used herein the term "composition" used herein means a physical mixture of two or more components.

All ranges recited herein include the endpoints and the terms "about", "from", "to" be construed as modifying a value they are applied to such that it is not absolute and includes, to the very least, the degree of expected experimental error, limitation of method or instrument error for a given technique used to measure the value.

As used herein, unless indicated otherwise, the term "isolated" or "isolation" refer to the subject compound as physically separated from the reaction mixture in which it is formed.

The term "elevated temperature" means the temperature from about 40° C. to about 120° C. In particular, from about 60° C. to about 100° C.

The term "cooling" means the reaction mixture is subjected to cooling at temperature from about 0° C. to about 35° C. In particular, from about 5° C. to about 30° C.

The term "crystallizing" herein means dissolving brexpiprazole obtained by the course of reaction or wet-cake or brexpiprazole obtained after drying, at a temperature from about 40° C. to reflux temperature of solvent or mixture thereof and cooling at an ambient temperature. In particular, the temperature from about 40° C. to about 150° C. and cooling at 0° C. to about 25° C.

The term "treating" means stirring, slurring, mixing, keeping that at any temperature or conditions.

The term "removing the solvents" may include, for example, one or more of filtration, filtration under vacuum, centrifugation, decantation, distillation and distillation under vacuum.

The term "substantially free" herein means brexpiprazole having each of SM-1, SM-2, impurity-S, impurity-T, and impurity-U less than about 0.15% by area percentage of HPLC. In particular, less than about 0.10% by area percentage of HPLC. More particular, less than about 0.05% by area percentage of HPLC. Most particularly, in the range of about 0.0% to about 0.05% by area percentage of HPLC.

The term "pure" herein refers to purity of brexpiprazole which is substantially free from one or more impurities and having purity of about 99% or more, of about 99.5% or more, particularly of about 99.9% or more by area percentage of HPLC.

The term "pharmaceutically acceptable" means that which is useful in preparing a pharmaceutical composition that is generally non-toxic and is not biologically undesirable, and includes that which is acceptable for veterinary use and/or human pharmaceutical use.

The term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

In one general aspect, there is provided brexpiprazole having a purity of about 99.5% or more by area percentage of HPLC.

In another general aspect, there is provided brexpiprazole having total impurities not more than 0.5% relative to brexpiprazole as measured by area percentage of HPLC.

In another general aspect, there is provided brexpiprazole having less than 0.1% 1-(benzo[b]thiophen-4-yl)piperazine or a salt thereof relative to brexpiprazole by area percentage of HPLC.

In general, the brexpiprazole is having less than 0.1% 1-(benzo[b]thiophen-4-yl)piperazine hydrochloride having Formula (V) relative to brexpiprazole by area percentage of HPLC.

In another general aspect, there is provided brexpiprazole substantially free from one or more of 7-(4-(4-(benzo[b]thiophen-4-yl)piperazin-1-yl)butoxy)-1-(4-(4-(benzo[b]-thiophen-4-yl)piperazin-1-yl)butyl)quinolin-2(1H)-one (impurity-S); 2,7-bis(4-(4-(benzo[b]thiophen-4-yl)piperazin-1-yl)butoxy)quinoline (impurity-T); or 7-(4-(4-(benzo[b]thiophen-4-yl)piperazin-1-yl)butoxy)-1,2-dihydroquinoline (impurity-U), relative to brexpiprazole by area percentage of HPLC.

In another general aspect, there is provided brexpiprazole having a purity of about 99.5% or more, by area percentage of HPLC which is crystallized from toluene.

In another general aspect, there is provided brexpiprazole which is substantially free from residual solvents.

In general, the term "substantially free from residual solvents" herein means residual solvents are within the permissible ICH limits suitable for pharmaceutical preparations. For example but not limited to less than 0.5%, particularly less than 0.3% or more particularly less than 0.2%, or most particularly not in detectable amount.

In another general aspect, there is provided brexpiprazole substantially free from residual solvent comprising crystallizing brexpiprazole in one or more solvents.

In general, the solvent comprises one or more of water, methanol, ethanol, isopropanol, butanol, acetone, methyl ethyl ketone, methyl isobutylketone, ethyl acetate, isopropyl acetate, butyl acetate, tetrahydrofuran, 1,4-dioxane, N,N-dimethylformamide, N,N-dimethyl acetamide, dimethylsulfoxide, 1,3-dimethyl-2-imidazolidinone (DMI) or acetonitrile or mixture thereof. In particular, the mixture of tetrahydrofuran and methanol may be used.

In another general aspect, brexpiprazole is stored under nitrogen atmosphere and packed in a double polyethene bag tied with a thread, keeping primary packing containing brexpiprazole inside a another polyethylene bag containing oxygen busters or desiccant and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

Impurities in brexpiprazole are undesirable, and, may be harmful to a patient being treated with a dosage form of the API in which a sufficient amount of impurities are present. Furthermore, the undesired impurities reduce the level of the API available in the pharmaceutical composition.

The ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process. The United States Food and Drug Administration guidelines recommend that the amounts of impurities be limited to less than 0.1 percent.

Generally, side products, by-products, and adjunct reagents (collectively "impurities") are identified by chromatographic methods, spectroscopically and with another physical methods, and then associated with a peak position, such as that in a chromatogram or a spot on a TLC plate, reported in Strobel p. 953, Strobel, H. A.; Heineman, W. R., Chemical Instrumentation: A Systematic Approach, 3rd ed. (Wiley & Sons: New York 1989).

In general, the brexpiprazole when prepared by the process disclosed in the prior art provides higher level of impurities. For example, the process disclosed in US '362 B2 provides the brexpiprazole with a purity of 91.82%. The impurity profile is tabulated in Table-1 based on the experiment as per reference example-15. The purification of brexpiprazole was performed using the process disclosed in US '362 B2. The purity of 95.11% was obtained with higher level of impurities. The impurity profile is tabulated in Table-2 based on the experiment as per reference example-16.

TABLE 1

Purity of Brexpiprazole as per reference example-15

| Sr. No. | Area % | R.R.T. | Peak Name |
|---|---|---|---|
| 1 | 0.02 | 0.16 | SM-2 |
| 2 | 0.24 | 0.18 | Unk |
| 3 | 0.11 | 0.25 | Unk |
| 4 | 1.96 | 0.53 | SM-1 |
| 5 | 0.02 | 0.72 | Spirocyclic compound |
| 6 | 0.29 | 0.77 | Unk |
| 7 | 91.82 | 1.00 | Brexpiprazole |
| 8 | 0.32 | 1.15 | Unk |
| 9 | 0.14 | 1.31 | Unk |
| 10 | 0.16 | 1.64 | Unk |
| 11 | 4.57 | 1.67 | Unk |

TABLE 2

Purity of Brexpiprazole as per reference example-16

| Sr. No | Area % | R.R.T. | Peak Name |
|---|---|---|---|
| 1 | ND | 0.16 | SM-2 |
| 2 | 0.06 | 0.19 | Unk |
| 3 | 0.03 | 0.26 | Unk |
| 4 | 1.00 | 0.51 | SM-1 |
| 5 | ND | 0.72 | Spirocyclic compound |
| 6 | ND | 0.77 | Unk |
| 7 | 95.11 | 1.00 | Brexpiprazole |
| 8 | 0.21 | 1.18 | Unk |
| 9 | 0.04 | 1.32 | Unk |
| 10 | 0.16 | 1.65 | Unk |
| 11 | 2.81 | 1.71 | Unk |

In another general aspect, there is provided brexpiprazole having purity of about 99.5% and having total impurities less than 0.5% by area percentage of HPLC, when prepared by the process of the present invention. The impurity profile is tabulated in Table-3 and Table-4 based on the experiments as per example-14.

TABLE 3

Purity of Brexpiprazole as per example-14

| Sr. No. | Area % | R.R.T. | Peak Name |
|---|---|---|---|
| 1 | ND | 0.16 | SM-2 |
| 2 | ND | 0.19 | Unk |
| 3 | ND | 0.26 | Unk |
| 4 | ND | 0.51 | SM-1 |
| 5 | 0.01 | 0.71 | Spirocyclic compound |
| 6 | 0.02 | 0.74 | Unk |
| 7 | 95.94 | 1.00 | Brexpiprazole |
| 8 | ND | 1.18 | Unk |
| 9 | 0.14 | 1.32 | Unk |
| 10 | 1.25 | 1.65 | Imp-S |
| 11 | 0.01 | 1.69 | Unk |
| 12 | 1.38 | 1.81 | Imp-T |

TABLE 4

Purity of Brexpiprazole (after purification) as per example-14

| Sr. No. | Area % | R.R.T. | Peak Name |
|---|---|---|---|
| 1 | ND | 0.16 | SM-2 |
| 2 | ND | 0.19 | Unk |
| 3 | ND | 0.26 | Unk |
| 4 | ND | 0.51 | SM-1 |
| 5 | ND | 0.71 | Spirocyclic compound |
| 6 | ND | 0.74 | Unk |
| 7 | 99.91 | 1.00 | Brexpiprazole |
| 8 | ND | 1.18 | Unk |
| 9 | ND | 1.32 | Unk |
| 10 | 0.02 | 1.62 | Imp-S |
| 11 | 0.01 | 1.69 | Unk |
| 12 | 0.02 | 1.77 | Imp-T |

SM-1: 1-(benzo[b]thiophene-4-yl)piperazine hydrochloride
SM-2: 7-hydroxyqunilin-2(1H)-one
Spirocyclic compound: 8-(benzo[b]thiophen-4-yl)-5, 8-diazaspiro[4.5]decan-5-iumbromide
Imp-S: 7-(4-(4-(benzo[b]thiophen-4-yl)piperazin-1-yl)butoxy)-1-(4-(4-(benzo[b]thiophen-4-yl)piperazin-1-yl)butyl)quinolin-2(1H)-one
Imp-T: 2,7-bis(4-(4-(benzo[b]thiophen-4-yl)piperazin-1-yl)butoxy)quinoline
ND: Not detected
Unk: Unknown In another general aspect, there is provided a composition comprising brexpiprazole and each of 7-(4-(4-(benzo[b]thiophen-4-yl)piperazin-1-yl)butoxy)-1-(4-(4-(benzo-[b]thiophen-4-yl)piperazin-1-yl)butyl)quinolin-2(1H)-one (impurity-S); 2,7-bis(4-(4-(benzo[b]thiophen-4-yl)piperazin-1-yl)butoxy)quinoline (impurity-T); or 7-(4-(4-(benzo[b]thiophen-4-yl)piperazin-1-yl)butoxy)-1,2-dihydroquinoline (impurity-U) in an amount less than about 0.15% relative to brexpiprazole by area percentage of HPLC.

In general, the impurities of brexpiprazole may be one or more of SM-1, SM-2, impurity-S, impurity-T or impurity-U represented by structural formula as herein below:

Impurity-U: 7-(4-(4-(benzo[b]thiophen-4-yl)piperazin-1-yl)butoxy)-1,2-dihydro-quinoline.

In another general aspect, there is provided a composition comprising brexpiprazole having 1-(benzo[b]thiophen-4-yl) piperazine or a salt thereof in an amount less than about 0.1% relative to brexpiprazole by area percentage of HPLC.

In another general aspect, there is provided composition comprising brexpiprazole having purity of about 99.5% or more and total impurities not more than 0.5%, by area percentage of HPLC.

In another general aspect, there is provided compound selected from one or more of 7-(4-(4-(benzo[b]thiophen-4-yl)piperazin-1-yl)butoxy)-1-(4-(4-(4-(benzo[b]thiophen-4-yl)piperazin-1-yl)butyl)quinolin-2(1H)-one; 2,7-bis(4-(4-(benzo[b]thiophen-4-yl)piperazin-1-yl)butoxy)-1,2-dihydroquinoline; or 7-(4-(4-(benzo[b]thiophen-4-yl)piperazin-1-yl)butoxy)-1,2-dihydroquinoline.

In another general aspect, there is provided brexpiprazole having particle size d90 of about 100 μm or less.

In general, the brexpiprazole of the present invention may be subjected to micronization for achieving the particle size d90 of about 100 μm or less.

In general, the brexpiprazole of the present invention is a crystalline anhydrous brexpiprazole.

In general, the crystalline anhydrous brexpiprazole is characterized by an X-ray powder diffraction pattern comprising peaks expressed in degrees 2θ (±0.2° 2θ) at 12.2°, 14.4°, 17.4°, 19.1°, 20.2°, 21.3° and 23.2±0.2° 2θ.

Figure 4:
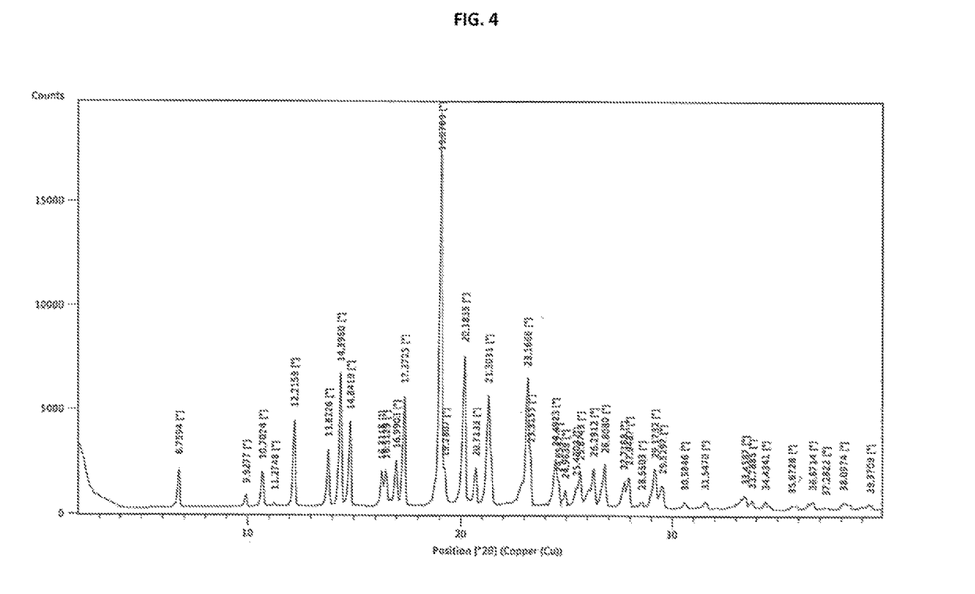
FIG. 4: Illustrates XRPD of crystalline anhydrous form of brexpiprazole.

In general, there is provided the anhydrous crystalline brexpiprazole having an X-ray powder diffraction pattern comprising peaks expressed in degrees 2θ (±0.2° 2θ) at 6.8°, 12.2°, 13.8°, 14.4°, 14.8°, 17.4°, 19.1°, 20.2°, 21.3° and 23.2±0.2° 2θ and having X-ray powder diffraction pattern substantially the same as that shown in FIG. 4.

Figure 5:
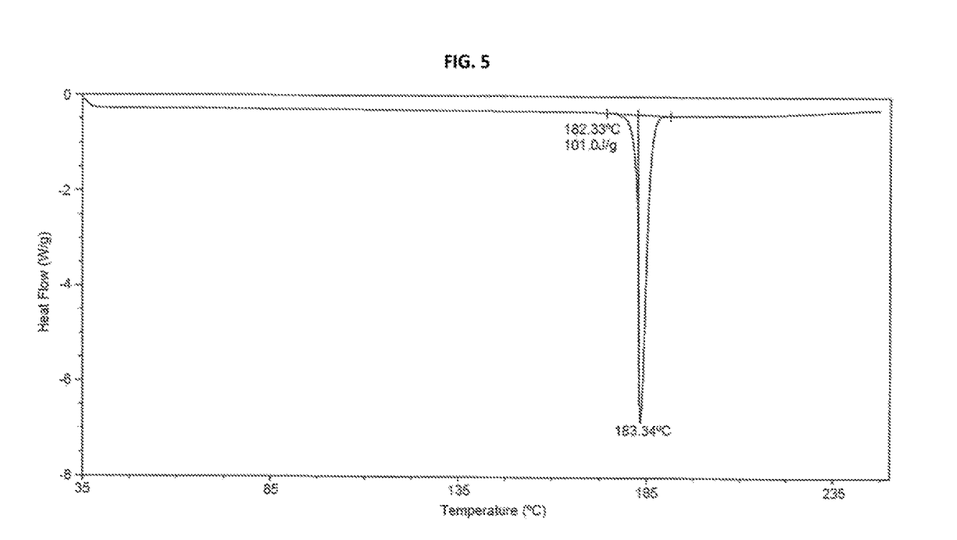
FIG. 5: Illustrates DSC of crystalline anhydrous form of brexpiprazole.

In general, there is provided the anhydrous crystalline brexpiprazole having a differential scanning calorimetry comprising endothermic peak at about 183±5° C. and differential scanning calorimetry substantially the same as that shown in FIG. 5.

In another general aspect, there are provided compounds selected from one or more of the following:

In general, the impurities of brexpiprazole may be one or more of SM-1 to impurity-U having nomenclature as under:

SM-1: 1-(benzo[b]thiophene-4-yl)piperazine hydrochloride

SM-2: 7-hydroxyqunilin-2(1H)-one

Impurity-S: 7-(4-(4-(benzo[b]thiophen-4-yl)piperazin-1-yl)butoxy)-1-(4-(4-(4-(benzo[b]thiophen-4-yl)piperazin-1-yl)butyl)quinolin-2(1H)-one;

Impurity-T: 2,7-bis(4-(4-(benzo[b]thiophen-4-yl)piperazin-1-yl)butoxy)quinoline;

In another general aspect, there is provided brexpiprazole having a purity of about 99.5% or more by area percentage of HPLC, prepared by a process comprising:

(a) reacting a compound 1-(benzo[b]thiophen-4-yl)piperazine hydrochloride of Formula (V) with 1,4-dibromobutane to obtain a spiro compound of Formula (III); and (b) reacting the spiro compound of Formula (III) with a compound 7-hydroxy-quinolin-2(1H)-one of Formula (II), to obtain the brexpiprazole.

In general, the reaction of compound of Formula (V) with 1,4-dibromobutane may be performed in the presence of a base in one or more solvents.

In general, the base in comprises one or more of alkali metal hydroxides selected from sodium hydroxide, potassium hydroxide, and lithium hydroxide; alkali metal carbonates selected from sodium carbonate, and potassium carbonate; sodium amide, sodium hydride, potassium hydride, sodium methoxide and potassium methoxide; organic bases selected from diethylamine, diisopropylethylamine, triethylamine, pyridine, quinoline, piperidine, morpholine, DBU and DABCO. In particular, sodium carbonate or potassium carbonate may be used.

The solvent for the reaction may be selected from water, tetrahydrofuran, dioxane, diethyl ether, benzene, toluene, xylene, methanol, ethanol, isopropanol, acetone, methyl ethyl ketone, N,N-dimethylformamide, N,N-dimethylacetamide, dimethylsulfoxide, 1,3-dimethyl-2-imidazolidinone (DMI) or acetonitrile or mixture thereof. In particular, methanol can be used.

In general, the reaction in step (b) may be performed in the presence of organic or inorganic base as mentioned herein above and in the presence or absence of catalyst in one or more solvents.

The solvents in step (b), comprises one or more of water, tetrahydrofuran, dioxane, diethyl ether, benzene, toluene, xylene, methanol, ethanol, isopropanol, acetone, methyl ethyl ketone, N,N-dimethylformamide, N,N-dimethyl acetamide, dimethylsulfoxide, 1,3-dimethyl-2-imidazolidinone (DMI) or acetonitrile or mixture thereof. In particular, the reaction is performed in N,N-dimethylformamide and using potassium carbonate as a base.

In another general aspect, the brexpiprazole obtained in step (b) is crystallized from toluene.

In another general aspect, there is provided a process for the preparation of brexpiprazole, the process comprising:
(a) reacting a compound 7-(4-hydroxybutoxy)quinoline-2-(1H)-one of Formula (X) with an oxidizing agent to prepare a compound of Formula (A); and (b) reacting the compound of Formula (A) with a compound 1-(benzo[b]thiophen-4-yl)piperazine of Formula (B), to obtain the brexpiprazole.

In general, the oxidizing agent in step (a) comprises one or more of DMSO and oxalyl chloride, pyridinium chlorochromate, sodium hypochlorite with (2,2,6,6-tetramethylpiperidin-1-yl)oxidanyl (TEMPO) or potassium permanganate.

The solvents in step (a) comprises of one or more of dichloromethane, dichloroethane, carbon tetrachloride, toluene or mixture thereof.

The reductive amination reaction in the step (b) is carried out in the presence of Raney Ni or Pd/C catalyst under nitrogen atmosphere and the solvent for the reaction can be selected from water, $C_1$-$C_4$-alcohols or mixture thereof.

In another general aspect, there is provided a process for the preparation of brexpiprazole, the process comprising:
(a) reacting a compound 7-hydroxyquinolin-2-(1H)-one of Formula (II) with a compound of Formula (S) to obtain a compound of Formula (R);

wherein X is OH, Cl, Br, I, —OCOCH₃.

(b) reacting the compound of Formula (R) with bis-(2-chloroethyl)amine hydrochloride of Formula (Q) to obtain a compound of Formula (P); and (c) reacting the compound of Formula (P) with benzo[b]thiophen-4-amine to obtain the brexpiprazole.

In general, the reaction in step (a) may be performed in the presence of a base selected from one or more of sodium hydroxide, potassium hydroxide or sodium carbonate.

The solvent for the reaction comprises one or more of methylethylketone, N,N-dimethylformamide, ethyl acetate, $C_1$-$C_4$-alcohol or mixture thereof.

In general, the reaction in the step (b) is performed in solvents comprises one or more of toluene, mix xylene, N-Methyl-2-pyrrolidone, dioxane, diethyl ether, benzene, N,N-dimethylformamide, dimethylsulfoxide or acetonitrile or mixture thereof. In particular, N,N-dimethylformamide may be used.

In general, the base for the reaction in step (b) comprises one or more of alkali metal hydroxides selected from sodium hydroxide, potassium hydroxide, and lithium hydroxide; alkali metal carbonates selected from sodium carbonate, and potassium carbonate; sodium amide, sodium hydride, potassium hydride, sodium methoxide and potassium methoxide; organic bases selected from diethylamine, diisopropylethylamine, triethylamine, pyridine, quinoline, piperidine, morpholine, DBU and DABCO. In particular, sodium carbonate or potassium carbonate may be used.

The reaction of the compound of Formula (P) with benzo[b]thiophen-4-amine in the step (c) may be performed in one or more solvents selected from n-butanol, toluene or mix xylene.

In another general aspect, there is provided processes for the preparation of brexpiprazole as shown in the following general reaction scheme (I):

-continued

In general, the compound of the Formula (A) can be prepared by the reaction scheme (V) as shown below:

wherein X is OH, Cl, Br, I, —OCOCH₃.

Polymorphic forms of a drug substance are characterized by a many methods including, for example, X-ray powder diffraction, microscopy, thermal analysis (e.g. differential scanning calorimetry, thermal gravimetric analysis and hot-stage microscopy), spectroscopy (e.g., near infrared (NIR), infrared (IR) and Raman, solid-state nuclear magnetic resonance (ss NMR)), and single crystal X-ray diffraction.

In another general aspect, there is provided a crystalline Form A of brexpiprazole and process for the preparation thereof.

In another general aspect, there is provided a crystalline form of brexpiprazole designated as Form A, is characterized by x-ray powder diffraction pattern having characteristic peaks expressed in terms of 2θ at about 14.1°, 14.4°, 17.4°, 19.1°, 20.2°, 23.0° and 23.2° 2θ±0.2° 2θ.

The Form A of brexpiprazole is further characterized by x-ray powder diffraction pattern having characteristic peaks expressed in terms of 2θ at about 6.7°, 10.7, 12.2°, 13.8°, 14.8°, 16.4°, 16.5°, 17.0°, 20.7°, 21.3°, 24.6°, 26.7°, 27.7°, 27.9°, 29.2°, 29.5°, 33.3° and 33.5° 2θ±0.2° 2θ.

Figure 1:
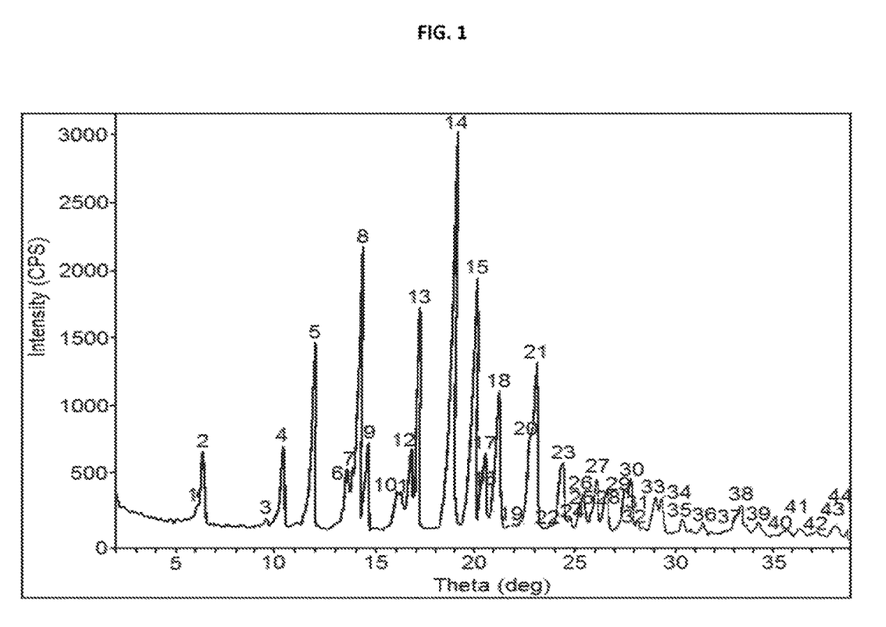
FIG. 1: Illustrates a powder x-ray diffraction pattern of crystalline Form A of brexpiprazole.
Figure 2:
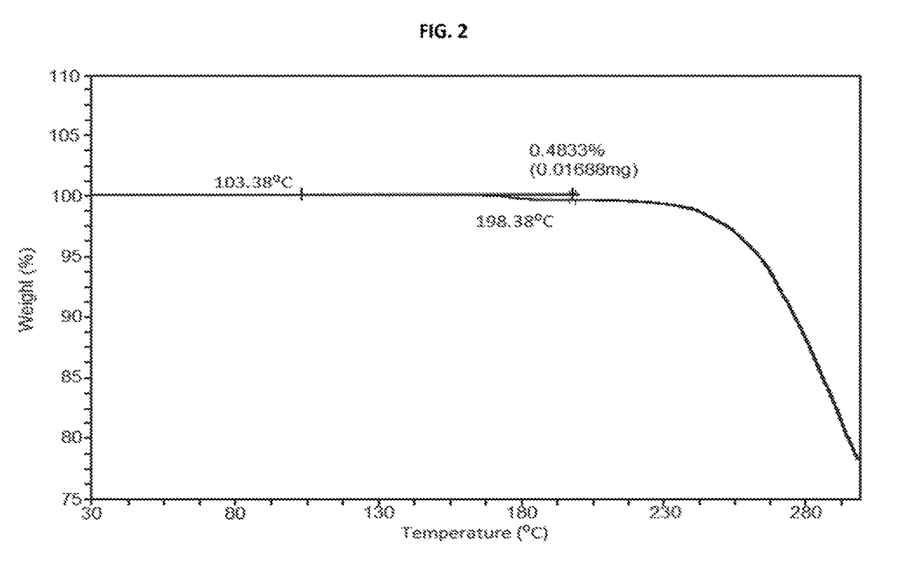
FIG. 2: Illustrates thermogravimetric analysis (TGA) of crystalline Form A of brexpiprazole.

In another general aspect, there is provided crystalline Form A of brexpiprazole characterized by X-ray powder diffraction substantially as same as shown in FIG. 1 and thermogravimetric analysis (TGA) substantially as same as shown in FIG. 2.

In another general aspect, there is provided a process for the preparation of crystalline Form A of brexpiprazole, the process comprising:
(a) treating brexpiprazole with one or more solvents to obtain a reaction mixture;
(b) stirring the reaction mixture at an elevated temperature;
(c) cooling the reaction mixture to obtain brexpiprazole;
(d) optionally washing the brexpiprazole with one or more solvents; and
(e) drying to obtain crystalline Form A of brexpiprazole.

In general, the solvents for the step (a) and (d) is selected from water, methanol, ethanol, isopropanol, and butanol or mixture thereof. In particular, water or ethanol or mixture thereof may be used.

The product can be isolated by removing the solvent using various techniques known in the art, for example, by filtration, decantation, centrifugation, filtration under vacuum, distillation and distillation under vacuum.

In general, the drying in the step (f) is performed using a hot air oven or vacuum oven.

In another general aspect, there is provided a crystalline Form B of brexpiprazole and process for the preparation thereof.

In another general aspect, the crystalline Form B of brexpiprazole is characterized by x-ray powder diffraction pattern having characteristic peaks expressed in terms of 2θ at about 5.7°, 12.1°, 12.6°, 14.3°, 19.0° and 20.0° 2θ±0.2° 2θ.

In general, the Form B of brexpiprazole is further characterized by x-ray powder diffraction pattern having characteristic peaks expressed in terms of 2θ at about 6.7°, 10.6°, 13.7°, 14.8°, 15.8°, 16.4°, 16.8°, 17.0°, 17.3°, 21.1°, 21.2°, 22.2°, 22.7°, 23.2° and 29.2° 2θ±0.2° 2θ.

Figure 3:
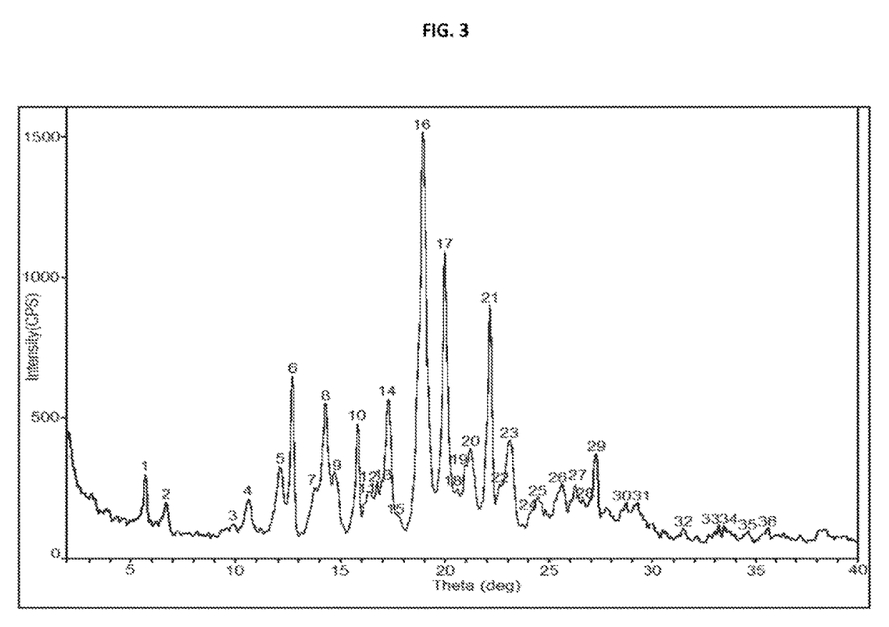
FIG. 3: Illustrates a powder x-ray diffraction pattern of crystalline Form B of brexpiprazole.

In another general aspect, there is provided crystalline Form B of brexpiprazole characterized by X-ray powder diffraction substantially as same as shown in FIG. 3.

In another aspect, there is provided a process for the preparation of crystalline Form B of brexpiprazole, the process comprising:
(a) reacting 7-(4-chlorobutoxy)-1H-quinolin-2-one with 1-benzo[b]thiophene-4-yl-piperazine hydrochloride in the presence of a base to obtain a reaction mixture;
(b) stirring the reaction mixture at 75-95° C.;
(c) cooling the reaction mixture;
(d) treating the reaction mixture with water to obtain brexpiprazole; and
(e) drying to obtain crystalline Form B of brexpiprazole.

In general, the base in step (a) comprises of alkali metal hydroxides selected from sodium hydroxide, potassium hydroxide, cesium hydroxide, and lithium hydroxide; alkali metal carbonates selected from sodium carbonate, potassium carbonate, cesium carbonate, and lithium carbonate; alkaline metal bicarbonates selected from lithium bicarbonate, sodium bicarbonate, and potassium bicarbonate; sodium amide, sodium hydride, potassium hydride, sodium methoxide, sodium ethoxide, potassium methoxide, and potassium ethoxide; organic bases selected from diethylamine, diisopropylethylamine, triethylamine, pyridine, quinoline, piperidine, morpholine, DBU and DABCO. In particular, potassium carbonate may be used.

The reaction can be performed with or without solvent or in an inert solvent.

The solvent for the reaction comprises one or more of water, tetrahydrofuran, dioxane, diethyl ether, benzene, toluene, xylene, methanol, ethanol, isopropanol, acetone, methyl ethyl ketone, N,N-dimethylformamide, dimethylsulfoxide or acetonitrile or mixture thereof. In particular, N,N-dimethylformamide can be used.

Powder X-ray Diffraction of crystalline Forms of brexpiprazole can be obtained under following conditions:

| Instrument | X-Ray Diffractometer, D/Max-2200/PC, Make: Rigaku or equivalent |
|---|---|
| X-Raysource | Cu/40 kv/40 mA |
| Diverging Slit | 1° |
| Scattering Slit | 1° |
| Receiving Slit | 0.15 mm |
| Monochromator RS | 0.8 mm |
| Counter | Scintillation Counter |
| Scam Mode | Continuous |
| Scan Speed | 3.000°/min |
| Sampling Width | 0.020° |
| Scan Axes | Two Theta vs cps |
| Scam Range | 2° to 40.0° |
| Theta Offset | 0.000° |

Thermogravimetric Analysis (TGA) was obtained using TA Instruments Q500 (TGA) Thermogravimetric analyzer.

In another general aspect, there are provided crystalline Forms A and B of brexpiprazole which are stable during storage and drying.

In another general aspect, the stable crystalline Form A or crystalline Form B of brexpiprazole are stored under nitrogen atmosphere and packed in a double polyethene bag tied with a thread, keeping primary packing containing crystalline Form A or Form B of brexpiprazole inside a another polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

In another general aspect, there is provided a pharmaceutical composition comprising pure brexpiprazole and one or more pharmaceutically acceptable carriers, excipients or diluents.

In another general aspect, there is provided a pharmaceutical composition comprising brexpiprazole together with one or more pharmaceutically acceptable carriers, excipients or diluents.

In another general aspect, there are provided brexpiprazole having purity of about 99% or more by area percentage of HPLC. In particular, the purity of about 99.6% or more, more particularly, the purity of about 99.8% or more, further more particularly, the purity by HPLC of about 99.9% or more, when measured by area percentage of HPLC.

The pharmaceutical composition of the present invention may be in the form of a solid or liquid dosage forms for oral, parenteral or topical use and may have immediate or sustained release characteristics. The dosage forms possible include powders, granules, creams, tablets, capsules, injectable, solutions, elixirs or suspensions.

The examples are set forth to aid in understanding the invention but are not intended to, and should not be construed to limit its scope in any way. The examples do not include detailed descriptions of conventional methods. Such methods are well known to those of ordinary skill in the art and are described in numerous publications.

EXAMPLES

Example-1: Preparation of 7-(4-chlorobutoxy)quinolin-2(1H)-one

In a round bottom flask, 5.0 g of 7-hydroxyquinolin-2(1H)-one, 6.42 g K₂CO₃ and 25 ml acetone were taken and stirred for 30 minutes at 25-35° C. 5.89 g 1-bromo-4-chloro butane was added into the reaction mixture and stirred for 5-6 hours at 50-55° C. After completion of the reaction, the reaction mixture was cooled to 25-35° C. The reaction mixture was filtered. The solvent was removed by distillation under vacuum. The solid was dried in a hot air oven at 45-50° C. to obtain 7-(4-chlorobutoxy) quinolin-2(1H)-one. Yield: 85%.

Example-2: Preparation of 7-(4-(bis-(2-chloroethyl) amino) butoxy) quinolin-2(1H)-one

In a round bottom flask, 7.0 g 7-(4-chlorobutoxy) quinolin-2(1H)-one, 7.66 g K$_2$CO$_3$ and 20 ml DMF were taken at 25-35° C. Sodium iodide was added in a catalytic amount and the reaction mixture was stirred for 30 minutes at 25-35° C. 5.92 g of bis-2-chloroethylamine was added into the reaction mixture at 25-35° C. The reaction mixture was stirred at 80-110° C. for 9-10 hours. After completion of the reaction, the reaction mixture was cooled to 25-35° C. and added into 100 ml water. The reaction mixture was stirred for 30 minutes at 20-30° C., then filtered and washed with water. The solid thus obtained was dried in a hot air oven at 45-50° C. to obtain 7-(4-(bis-(2-chloroethyl) amino) butoxy) quinolin-2(1H)-one. Yield: 86%.

Example-3: Preparation of Brexpiprazole

In a round bottom flask, 5.0 g 7-(4-(bis (2-chloroethyl) amino) butoxy) quinolin-2(1H)-one, 20 ml n-butanol were taken at 25-35° C. 2.29 g benzo[b]thiophen-4-amine was added into the reaction mixture at 25-35° C. The reaction mixture was stirred at 110-125° C. After completion of the reaction, the reaction mixture was cooled to 20-25° C. and filtered and washed with toluene. The solid was dried in a hot air oven at 45-50° C. to obtain brexpiprazole. The brexpiprazole can be purified by isopropanol and water. Yield: 90%.

Example-4: Preparation of 7-(4-hydroxybutoxy) quinolin-2(1H)-one

In a round bottom flask, 5.0 g of 7-hydroxyquinolin-2 (1H)-one, 7.5 g K$_2$CO$_3$ and 25 ml DMF were taken at 25-35° C. The reaction mixture was stirred for 30 minutes at 25-35° C. 3.70 g of 4-chloro butane-1-ol was added and the reaction mixture was stirred at 70-75° C. for 9-10 hours. After completion of the reaction, the reaction mixture was cooled to 25-35° C. and added into water and stirred for 10-15 minutes. The solid was filtered and washed with water and dried in a hot air oven at 45-50° C. to obtain 7-(4-hydroxybutoxy) quinolin-2(1H)-one. Yield: 80%.

Example-5: Preparation of 4-((2-oxo-1,2-dihydroquinolin-7-yl) oxy) butanal

In a round bottom flask, 5.0 g of 7-(4-hydroxybutoxy) quinolin-2(1H)-one, 9.89 g pyridinium chlorochromate (PCC) and 50 ml dichloromethane were taken at 25-30° C. The reaction mixture was cooled to 10-20° C. A solution of 5.0 g 7-(4-hydroxy butoxy) quinolin-2(1H)-one in 50 ml dichloromethane was added into the reaction mixture at 10-20° C. The reaction mixture was stirred for 2 hours at 10-20° C. After completion of the reaction, 50 ml water was added into the reaction mixture and stirred for 30 minutes at 10-30° C. Organic and aqueous layers were separated and organic layer was washed with 10% sodium bicarbonate solution and then washed with water. The organic solvent was distilled out under vacuum to obtain 4-((2-oxo-1, 2-dihydroquinolin-7-yl)oxy)butanal.

Example-6: Preparation of Brexpiprazole

5.0 g of 4-((2-oxo-1, 2-dihydroquinolin-7-yl) oxy) butanal, 4.72 g of 1-(benzo[b]thiophen-4-yl) piperazine and 50 ml methanol were taken in an autoclave at 25-30° C. 1.0 g Raney Ni catalyst was added into that under nitrogen atmosphere. The reaction mixture was stirred at 50-55° C. for 4-5 hours at 5.0 Kg of hydrogen pressure. After completion of the reaction, the reaction mixture was cooled to 20-30° C. and filtered. The solvent was removed by distillation under vacuum. The solid was crystallized using ethanol and water and dried for 5-6 hours at 50-55° C. to obtain brexpiprazole.

Example-7: Preparation of Compound of Formula (Y)

In a round bottom flask, 5.0 g of 7-hydroxyquinolin-2 (1H)-one, 7.5 g K$_2$CO$_3$ and 25 ml DMF were taken at 25-35° C. and the reaction mixture was stirred for 30 minutes at 25-35° C. 5.20 g 4-chloro-1,1-dimethoxybutane was added into the reaction mixture and stirred for 10 hours at 70-75° C. After completion of the reaction, the reaction mixture was cooled to 25-35° C. and added into water. The solid was filtered and washed with water and dried in a hot air oven at 45-50° C. to obtain compound of the Formula (Y). Yield: 80%.

Example-8: Preparation of Compound of Formula (A)

In a round bottom flask, 5.0 g compound of the Formula (Y) was taken in 25 ml methanol. 3.0 ml dilute HCl was added at 25-35° C. and stirred for 8 hours at 25° C. to 35° C. After completion of the reaction, the water and ethyl acetate was added into the reaction mixture. The layers were separated and solvent was removed under reduced pressure from the organic layer to obtain the compound of Formula (A).

Example-9: Preparation of Compound of Formula (III)

In a round bottom flask, 25.0 g 1-(benzo[b]thiophen-4-yl) piperazine hydrochloride, 22.9 g Na$_2$CO$_3$ and 125 ml methanol were taken at 25-35° C. The reaction mixture was stirred for 5 minutes at 25-35° C. 23.10 g 1, 4-dibromo butane was added and the reaction mixture was stirred for 7-8 hours at 55-60° C. After completion of the reaction, the reaction mixture was cooled to 25-35° C. and then filtered and washed with 25 ml methanol. The solvent of the reaction mixture was concentrated and 5 volume of acetone was added into the reaction mixture and stirred for 30 minutes at 25-35° C. The reaction mixture was filtered and dried to obtain compound of Formula (III). Yield: 80%.

Example-10: Preparation of Brexpiprazole

In a round bottom flask, 1.0 g spiro compound of Formula (III), 0.45 g 7-Hydroxy-2(1H)-quinolin-one, 0.59 g potassium carbonate, 25 mg 18-crown-6-ether and 5 ml dimethyl formamide were added at 25-35° C. The reaction mixture was stirred at 125-130° C. After completion of the reaction, the reaction mixture was cooled to 25-35° C. and added into 50 ml water. The product was extracted using 30 ml toluene. The toluene layer was washed with water and treated with charcoal. After charcoal treatment, the toluene layer was concentrated and ethanol was added into that and the solid was isolated and dried to obtain brexpiprazole with 80% yield.

Example-11: Preparation of Crystalline Form A of Brexpiprazole

In a round bottom flask, 1.5 gm brexpiprazole, 15 ml ethanol and 10 ml water were mixed at 25-35° C. The reaction mixture was heated to 75-80° C. and stirred for 30 minutes. The reaction mixture was cooled to 25-30° C. and stirred for 30 minutes. The solid was filtered and the wet cake was washed with 4 ml mixture of ethanol and water. The product was dried in a hot air oven at 50-55° C. to obtain crystalline Form A of brexpiprazole.

Example-12: Preparation of Crystalline Form B of Brexpiprazole

In a 250 ml round bottom flask, 1.23 gm 1-benzo[b]-thiophene-4-yl-piperazine HCl, 0.68 gm $K_2CO_3$ and 5 ml DMF were taken and the reaction mixture was stirred at 25-35° C. for half an hour. 1 gm 7-(4-chlorobutoxy)-2(1H) quinolinone was added into the reaction mixture and the reaction mixture was stirred for 3 hours at 80-90° C. After completion of the reaction, the reaction mixture was cooled to 25-35° C. The reaction mixture was added into 25 ml water and stirred at 25-35° C. for an hour. The product was filtered under vacuum and washed with water. The product was dried in hot air oven at 45-50° C. to obtain crystalline Form B of brexpiprazole.

Example-13: Preparation of Compound of Formula (III)

In a round bottom flask, 100 g 1-(benzo[b]thiophen-4-yl) piperazine hydrochloride, 79 g $Na_2CO_3$ and 200 ml methanol were taken at 25-35° C. 93.2 g 1,4-dibromobutane and 25 ml methanol were added and the reaction mixture was stirred for 2 hours at 55-65° C. After completion of the reaction, the reaction mixture was cooled to 20-25° C. and then filtered and washed with 50 ml methanol. The filtrate was taken in another flask and the solvent was removed by distillation at 65-75° C. 200 ml water and 100 ml toluene were added and stirred for 30 minutes to an hour at 25-35° C. The reaction mass was filtered and washed using water and toluene and then dried to obtain compound of Formula (III). Yield: 97.82%.

Example-14: Preparation of Brexpiprazole

In a round bottom flask, 100 g spiro compound of Formula (III), 43 g $K_2CO_3$ and 800 ml DMF were taken. 50.2 g 7-Hydroxy-2(1H)-quinolin-one, was added and the reaction mixture was stirred at 130-135° C. for 6-9 hours. After completion of the reaction, the reaction mixture was cooled to 80-90° C. and 100 ml toluene was added into that and stirred for 10 minutes. 1060 ml water was added slowly and the reaction mixture was stirred for an hour at 25-35° C. The solid was filtered and washed with 50 ml pre-cooled toluene. The wet cake was then washed with 100 ml water and dried to obtain brexpiprazole having purity of 95.94%.

The crude wet product was taken in 1000 ml toluene in another flask and stirred at 90-100° C. 5 g activated charcoal was added and stirred at 105-110° C. for 15 minutes. The reaction mixture was filtered through hyflo bed and washed using toluene. The filtrate was again stirred for 10 minutes at 105-110° C. and then cooled to 20-25° C. The reaction mass was filtered and washed with toluene. The wet cake was dried in hot air oven for 6 hours. The dry material was taken in another flask and treated with 360 ml THF and 225 ml methanol at below 70° C. to make a clear solution. The solvent was distilled out and 225 ml methanol was also added simultaneously at below 70° C. The reaction mixture was cooled and then filtered and washed with 45 ml methanol and dried under vacuum to obtain 82% brexpiprazole having purity 99.91%.

Impurity Profile:

SM-1: ND; SM-2: ND; Imp-S: 0.02; Imp-T: 0.02; Imp-U: ND.

Reference Example-15: Preparation of Brexpiprazole as Per U.S. Pat. No. 7,888,362 B2 (Example-1)

In a round bottom flask, 50 g 7-(4-chlorobutoxy)-quinolin-2(1H)-one, 55.55 g 1-(benzo[b]thiophen-4-yl)piperazine hydrochloride, 77.77 g $K_2CO_3$, 33.33 g NaI and 500 ml dimethyl formamide were added and stirred for 2 hours at 80° C. and 1 hour for 90° C. The reaction mixture was quenched into 2500 ml water at 20-25° C. and stirred for 1 hour. The product was filtered, washed with water, and dried in hot air oven for 14 hours at 50° to 55° C. to obtain 88.2 g brexpiprazole having purity of 91.82%.

Reference Example-16: Purification of Brexpiprazole as Per U.S. Pat. No. 7,888,362 B2 (Example-1)

In a round bottom flask, 5 g brexpiprazole prepared in example-15 was dissolved in a mixture of 25 mL methylene dichloride and 25 mL methanol. The reaction mixture was filtered through hyflow, washed with mixture of methylene dichloride and methanol. The filtrate was dried over magnesium sulfate and distilled. The reaction mass was co-distilled with 10 mL ethanol. 50 mL ethanol was added to the residue and stirred for 30 minutes at 75-80° C., cooled to 25° C. and stirred for 60 minutes. The reaction mixture was filtered and the wet-cake was dried in hot air over to obtain 4.42 g brexpiprazole having purity of 95.11%.

While the present invention has been described in terms of its specific embodiments, certain modifications and equivalents will be apparent to those skilled in the art and are intended to be included within the scope of the present invention.

We claim:

1. A process for the preparation of brexpiprazole, the process comprising the steps of:
   (a) reacting compound 1-(benzo[b]thiophen-4-yl)piperazine hydrochloride of Formula (V) with 1,4-dibromobutane to obtain a spiro compound of Formula (III); and (b) reacting the spiro compound of Formula (III) with a compound 7-hydroxy-quinolin-2(1H)-one of Formula (II), to obtain the brexpiprazole.

2. The process according to claim 1, wherein the brexpiprazole obtained in step (b) is crystallized from one or more solvents.

3. The process according to claim 2, wherein the solvent comprises one or more of water, methanol, ethanol, isopropanol, butanol, acetone, methyl ethyl ketone, methyl isobutylketone, ethyl acetate, isopropyl acetate, butyl acetate, tetrahydrofuran, 1,4-dioxane, N,N-dimethylformamide, N,N-methyl acetamide, dimethylsulfoxide, 1,3-dimethyl-2-imidazolidinone-(DMI), and acetonitrile, toluene, or a mixture thereof.

4. The process according to claim 1, wherein the brexpiprazole obtained in step (b) is crystallized from toluene.

5. An intermediate compound of Formula (III), for the preparation of brexpiprazole.

6. The process according to claim 2, wherein the brexpiprazole has one or more of impurities 7-(4-(4-(benzo[b]thiophen-4-yl)piperazin-1-yl)butoxy)-1-(4-(4-(benzo[b]thiophen-4-yl)piperazin-1-yl)butyl)quinolin-2(1H)-one (impurity-S); 2,7-bis(4-(4-(benzo[b]thiophen-4-yl)piperazin-1-yl)butoxy)quinoline (impurity-T); and 7-(4-(4-(benzo[b]thiophen-4-yl)piperazin-1-yl)butoxy)-1,2-dihydro-quinoline (impurity-U) from 0.0% to 0.05%, relative to brexpiprazole by area percentage of HPLC.

7. The process according to claim 1, wherein the brexpiprazole has 1-(benzo[b]thiophen-4-yl)-piperazine, or a salt thereof in an amount less than about 0.1% relative to brexpiprazole by area percentage of HPLC.

8. The process according to claim 1, wherein the brexpiprazole has a purity of 99.9% or more by area percentage of HPLC.

* * * * *